(12) United States Patent
Marshall et al.

(10) Patent No.: US 10,909,501 B2
(45) Date of Patent: *Feb. 2, 2021

(54) PET INSURANCE SYSTEM AND METHOD

(71) Applicant: Trupanion, Inc., Seattle, WA (US)

(72) Inventors: Kerri E. Marshall, Seattle, WA (US);
Darryl Rawlings, Seattle, WA (US);
Kathryn Plowman, Portland, ME (US);
Christopher Cappelletti, Carnation, WA (US)

(73) Assignee: Trupanion, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/023,624

(22) Filed: Jun. 29, 2018

(65) Prior Publication Data

US 2018/0349852 A1     Dec. 6, 2018

Related U.S. Application Data

(63) Continuation-in-part of application No. 14/924,606, filed on Oct. 27, 2015, now Pat. No. 10,013,530, which is a continuation-in-part of application No. 14/210,079, filed on Mar. 13, 2014.

(60) Provisional application No. 61/801,404, filed on Mar. 15, 2013.

(51) Int. Cl.
| | | |
|---|---|---|
| G06Q 10/10 | (2012.01) |
| G06Q 40/08 | (2012.01) |
| G16H 40/20 | (2018.01) |
| G16H 10/60 | (2018.01) |

(52) U.S. Cl.
CPC ............. *G06Q 10/10* (2013.01); *G06Q 40/08* (2013.01); *G16H 40/20* (2018.01); *G16H 10/60* (2018.01)

(58) Field of Classification Search
CPC ...................................................... G06Q 10/10
See application file for complete search history.

(56) References Cited

U.S. PATENT DOCUMENTS

| | | |
|---|---|---|
| 5,720,502 A | 2/1998 | Cain |
| 6,117,526 A | 9/2000 | Marks, I |
| 6,966,064 B1 | 11/2005 | Schneidewend et al. |
| 7,155,405 B2 | 12/2006 | Petrovich |
| 7,266,770 B2 | 9/2007 | Onbe et al. |
| D572,717 S | 7/2008 | Loehr et al. |

(Continued)

FOREIGN PATENT DOCUMENTS

| | | |
|---|---|---|
| JP | 2002073802 A | 3/2002 |
| JP | 2013022984 A | 2/2013 |

(Continued)

OTHER PUBLICATIONS

Co-pending U.S. Appl. No. 16/115,446, filed Aug. 28, 2018.

(Continued)

*Primary Examiner* — Reginald R Reyes
(74) *Attorney, Agent, or Firm* — Wilson Sonsini Goodrich & Rosati

(57) ABSTRACT

This disclosure relates to a system and method implemented to facilitate real-time medical coverage for veterinary hospitals. More specifically, the disclosure as a pet medical insurance system and method utilizes data available in veterinary hospital practice information systems to facilitate real-time insurance enrollment and claims processing.

19 Claims, 20 Drawing Sheets

(56) References Cited

U.S. PATENT DOCUMENTS

| | | | |
|---|---|---|---|
| 7,496,583 | B2 | 2/2009 | Moore et al. |
| D605,653 | S | 12/2009 | Danton |
| 7,711,660 | B1 | 5/2010 | Gentile et al. |
| 8,341,547 | B2 | 12/2012 | Ingman et al. |
| 8,359,605 | B2 | 1/2013 | Ross |
| D777,737 | S | 1/2017 | Marshall et al. |
| 10,013,530 | B2 | 7/2018 | Marshall et al. |
| 10,255,993 | B2 | 4/2019 | Marshall et al. |
| 2002/0099276 | A1 | 7/2002 | Schmidt et al. |
| 2003/0004740 | A1 | 1/2003 | Voutsas et al. |
| 2004/0254816 | A1 | 12/2004 | Myers |
| 2005/0060344 | A1 | 3/2005 | Pawlick |
| 2005/0091606 | A1 | 4/2005 | Sauermann |
| 2006/0074724 | A1* | 4/2006 | Schwartz ............... G06Q 50/24 705/4 |
| 2006/0075724 | A1 | 4/2006 | Kammler et al. |
| 2006/0196436 | A1 | 9/2006 | Nichols |
| 2006/0251775 | A1 | 11/2006 | Anderson et al. |
| 2007/0084099 | A1 | 4/2007 | Sarbo et al. |
| 2007/0203758 | A1* | 8/2007 | Stephens ............... G06Q 10/10 705/4 |
| 2008/0172617 | A1 | 7/2008 | Takeda et al. |
| 2008/0307339 | A1 | 12/2008 | Boro et al. |
| 2009/0106678 | A1 | 4/2009 | Chase et al. |
| 2009/0182586 | A1* | 7/2009 | Cohane ............... G06Q 20/102 705/4 |
| 2009/0289844 | A1 | 11/2009 | Palsgrove et al. |
| 2009/0300540 | A1 | 12/2009 | Russell |
| 2010/0017234 | A1 | 1/2010 | Stephens et al. |
| 2010/0293487 | A1 | 11/2010 | Schoenberg |
| 2011/0119574 | A1 | 5/2011 | Rogers et al. |
| 2011/0131507 | A1 | 6/2011 | Butcher |
| 2012/0060105 | A1 | 3/2012 | Brown et al. |
| 2012/0060216 | A1 | 3/2012 | Chaudhri et al. |
| 2012/0110453 | A1 | 5/2012 | Ma et al. |
| 2012/0265702 | A1 | 10/2012 | Maher |
| 2013/0073366 | A1 | 3/2013 | Heath |
| 2013/0218592 | A1 | 8/2013 | Hashmat |
| 2014/0155785 | A1 | 6/2014 | Haas |
| 2014/0278551 | A1 | 9/2014 | Marshall et al. |
| 2016/0364547 | A1 | 12/2016 | Love et al. |

FOREIGN PATENT DOCUMENTS

| | | |
|---|---|---|
| WO | WO-2006036316 A1 | 4/2006 |
| WO | WO-2014152179 A2 | 9/2014 |
| WO | WO-2017075207 A1 | 5/2017 |

OTHER PUBLICATIONS

European search report dated Dec. 9, 2016 for EP Application No. 14770490.
International search report with written opinion dated Nov. 29, 2016 for PCT/US2016/059095.
Notice of allowance dated May 17, 2018 for U.S. Appl. No. 14/924,606.
Notice of allowance dated May 29, 2018 for U.S. Appl. No. 14/924,606.
PCT/US2014/27042 International Search Report and Written Opinion dated Oct. 1, 2014.
U.S. Appl. No. 14/210,079 Final Office Action dated Sep. 5, 2017.
U.S. Appl. No. 14/210,079 Non-Final Office Action dated Dec. 7, 2016.
U.S. Appl. No. 14/210,079 Non-Final Office Action dated Mar. 21, 2018.
U.S. Appl. No. 14/924,606 Final Office Action dated Jul. 22, 2016.
U.S. Appl. No. 14/924,606 Final Office Action dated Oct. 12, 2017.
U.S. Appl. No. 14/924,606 Non-Final Office Action dated Jan. 12, 2017.
U.S. Appl. No. 14/924,606 Non-Final Office Action dated Mar. 10, 2016.
U.S. Appl. No. 29/449,619 Final Office Action dated Jul. 17, 2015.
U.S. Appl. No. 29/449,619 Non-Final Office Action dated Oct. 3, 2014.
U.S. Appl. No. 29/449,619 Notice of Allowance dated Sep. 13, 2016.
Notice of allowance dated Nov. 28, 2018 for U.S. Appl. No. 16/115,446.
Office action dated Jan. 18, 2019 for U.S. Appl. No. 14/210,079.
U.S. Appl. No. 14/210,079 Non-Final Office Action dated Sep. 6, 2019.
2011 Trupanion set up: pp. 15 to 17 https://mc9ljrfyiceiaeu2gdfotgw0-wpengine.netdna-ssl.com/wp-content/uploads/2019/09/AVImark-Release-Notes-2011.3.6.pdf, 25 pages.
2012 1st Annual Naphia Conference. Vetenvoy featured presenter. ("1st annual naphia summit_VE Described_Copied for Patent.pdf") 7 pages.
2012 ACT, 2008-9 PurinaCare. ("ACT Automated Claims Processing Feb. 2012 Proposal.doc") 9 pages.
Avimark 2011 announcement of offering ("Avimark_2011-Insurance Update.pdf") 1 page.
Avimark, ("Avimark-Release-Notes-2011.3.6.pdf") https://docplayer.net/63752091-Avimark-readme-table-of-contents-please-use-the-bookmark-menu-on-the-left-to-navigate-between-each-project-and-feature-1.html, 21 pages (accessed on Apr. 15, 2020).
Avimark, http://docplayer.net/11571437-Vpi-eclaim-equote-integration.html, 18 pages (accessed on Apr. 15, 2020).
Avimark Insurance and vetenvoy, https://www.petinsurance.com/images/VSSimages/landingPages/Vet_Envoy_AVImark/setup.pdf, 3 pages (accessed on Apr. 15, 2020).
Co-pending U.S. Appl. No. 16/779,338, filed Jan. 31, 2020.
"AVImark eClaims Instructions v2.0 for Trupanion.pdf", 22 pages (2012).
PracticeOn: https://cdn.website-editor.net/f8ec393e8489444b912f11c22465414a/files/uploaded/Connector%2520v101%2520Insuranc%2520Trials%2520Submission%2520Instructions%2520for%2520AVImark.pdf https://cdn.website-editor.net/f8ec393e8489444b912f11c22465414a/files/uploaded/Connector%2520v101%2520Insuranc%2520Trials%2520Submission%2520Instructions%2520for%2520AVImark.pdf, 7 pages (2018).
PracticeOn in the market in Canada. https://www.practiceon.com/connector-insurance-support, 2 pages (2019).
Request for Ex Parte Reexamination filed Mar. 2, 2020 (56 pages) for U.S. Appl. No. 90/020,134 by PracticeOn Limited.
Trupanion_Avimark_PracticeOn 2011 Flyer.https://drive.google.com/file/d/1DNh3EVeoUwXaeh3-rfsTIvxdppDXhiHj/view?ts=5e587265 ("Trupanion_Avimark_Vetenvoy Practice Flyer.pdf") 1 page.
Vetenvoy/Livetime 24/7 Public and Open API, Feb. 12, 2008 ("Vet Envoy Services API v1.50.pdf") http://www.vetenvoy.com/uk/content/vet%20envoy%20services%20api%20v1.50.pdf, 109 pages.
Vetenvoy's architecture, design and workflows. ("VE IT Topology.pdf") 5 pages (accessed on Apr. 15, 2020).
Vetenvoy in the press example, Dec. 2009 http://www.vetenvoy.com/uk/Content/VetEnvoy%20VBJ%20article.pdf, 4 pages.
Vetenvoy publicly shared information, Apr. 2009. https://veterinary-practice.com/article/a-giant-step-towards-the-paperless-office, 7 pages.
Vetenvoy.com information about eclaims, 2009. http://www.vetenvoy.com/, http://www.vetenvoy.com/, 2 pages.
Vetmessenger on 350+ practices 2012/13+0 https://vimeopro.com/4act/vetenvoy-messenger-client-software/video/66664634, 1 page.
Vetmessenger on 350+ practices 2012/13+ https://www.dropbox.com/s/pddxa0ecflrcch1/New%20Development%2004.23.2013%20VetMessenger.mp4?dl=0, 1 page.
VetXML Consortium ("vetxml_timeline page.docx") http://www.vetxml.co.uk/en/about-the-consortium/#about-the-consortium, 7 pages (2020).
U.S. Appl. No. 14/210,079 Office Action dated Jun. 10, 2020.
U.S. Appl. No. 16/779,338 Office Action dated May 28, 2020.
AVImark, now Covetrus Software Services, AVImark Release Notes Jan. 7, 2011, 75 pages https://softwareservices.covetrus.com/avimark-legacy-release-notes/, 2011.

(56) References Cited

OTHER PUBLICATIONS

Wikipedia, https://en.wikipedia.org/w/index.php?title=Plug_and_play&oldid=539757675, Plug and Play, Feb. 22, 2013.

* cited by examiner

FIG. 7 trupanion express

Search by pet name, owner last name, or phone number

Help

- Appointments
- Pets
- Claims
- Certificates
- Reports
- Start New Claim
- Offer Certificate

📞 000.733.2670
🌐 TRUPANION.COM

Offer Certificate

Mona Joy
Matt Schinbein & Pam

Phone: 5855855858

Email: TEST_Trupanion@Trupanion.com

Address: 5245 Seashore Ave NW

Address 2:

City: Seattle     State: WA

Zip: 98107

Gender: F ▼

Spayed or Neutered: Yes ▼

Breed: American Bulldog ▼

Age: 7 years old ▼

Hide Pet Details ∧

Certificate Details
Attending DVM: Robert Robertson, D ▼

Agreement
Matt Schinbein agree(s) to share their information, including email address with Trupanion
I am authorized on behalf of Juan de Fuca Veterinary Clinic to confirm that a comprehensive exam was give today, Oct 7th, to Mona Joy by attending DVM Robert Robertson, DVM Submitters Name: Test

[Send Offer]     Cancel Offer

| Show ○ All ● Last 30 days | | Sort by Issue Date ▽ ⬇ |
|---|---|---|
| Vargus<br>Brian Trenton<br>Email: briantrenton@test.com | Issued: 12/10/2014 | 21hrs<br>Status: Issued |
| Oberlin<br>Brian Trenton<br>Email: briantrenton@test.com | Issued: 12/10/2014 | 19hrs<br>Status: Issued |
| Sadie<br>Josh Logan<br>Email: joshlogan@test.com | Issued: 12/09/2014 | Status: Expired |
| Swoops<br>Tina & Mark Johnson<br>Email: tinaandmark@test.com | Issued: 12/09/2014 | Status: Expired |
| Liona<br>Stacy May<br>Email: stacymay@test.com | Issued: 12/09/2014 | Status: Expired |
| Hadley<br>Brian Trenton<br>Email: briantrenton@test.com | Issued: 12/09/2014 | Status: Activated |

FIG. 11A

| trupanion express* | Search by pet name, owner name, or phone number 🔍 | | | | | | Help ❓ |

| | Overdue ⏲ 2 | Needed Today 📅 4 | Needed Later 📅 10 | Open 👁 13 | Completed ☑ 65 | Expired ⏲ 3 | Cancelled ✕ 10 |

- 📅 Appointments
- 🐾 Pets
- 📋 Claims
- 🏷 Certificates
- 📊 Reports
- 📧 Request ④
- ▢ Start New Claim
- 🎁 Offer Certificate
- ☎ 855.266.2154
- ✉ trupanion.com Show ☑ Active ☐ Completed     Group by [Priority]  Sort by [Aging number] ⬇

⌄ Critical Claims ①

Rocky
Dan Smith & Danielle Smith

Status Requested    Full Medical History 06/01/2014-01/26/2015
Aging 2 hrs
Created 01/26/2015   Labs                Imaging
Poll TU0004637827    • Bloodwork         • Radiographs
Claim# C7489387      • Urinalysis        • Ultrasound
                     • Other: Lorem Ipsum • MRI
                                         • Other: Dolor Sitt

[Attach ⌄]
[Reply]
[Submit ⌄]

Collapse

💬 1 new   📎 2 attchments
📎 09212014_Rocky_Dansmith_DanielleSmith_Full_Med_Recs.Pdf    Remove
📎 09212014_Rocky_Dansmith_DanielleSmith_Full_Med_Recs.Pdf    Remove Show all 8 Comments ⌃

🏥 Elliot Bay Animal Hospital  Today at 8:03 AM
Please let us know if these are the right documents. We don't have any urinalysis work on file.

🐾 Margaret Powell  Today at 8:51 AM
Upgraded the priority to urgent since the owner has asked serval question about recent claims. Can you provide an update on the status?

🐾 Margaret Powell  Today at 9:30 AM
Actually, We are looking specifically for the medical records from 7/21. Can you send those to us at your earliest opportunity? We received another call from the owner. Dan smith, this morning.

Enter a response to Trupanion

[Send]

| trupanion express* | Search by pet name, owner last name, or phone number | | | Help ❓ |
|---|---|---|---|---|
| 📅 Appointments | 2:00 PM | Zeus<br>John & Mellissa Stuart<br>Start Claim | Waldo<br>John Oliver<br>Offer Certificate › | Sylvester<br>Theo Musiber<br>Offer Certificate › | Chunky Brewster<br>Juliette Potpell<br>Offer Certificate › | Toaster<br>Theo Crabapples<br>Claim Processed |
| 🐾 Pets | 2:30 PM | Hooch<br>Scott Turner<br>Offer Certificate › | Lady<br>Jim Dear<br>Offer Certificate › | Benji<br>Joe Camp<br>View Decision Approved | Carter<br>Brian Trenton<br>Offer Certificate › | Fang<br>Rubeus Hagrid<br>Offer Certificate › |
| 📄 Claims | 3:00 PM | Bear<br>Shirley Little<br>Offer Certificate › | Giada<br>Beatrice & John Singleton<br>Offer Certificate › | Mouse<br>Dellah Hart<br>Offer Certificate › | Oberlin<br>Brian Trenton<br>Start Claim | Elf<br>Josephine<br>Offer Certificate › |
| 🏆 Certificates | 3:30 PM | Ricky<br>Ralph McMann<br>Certificate Offered | Rose<br>Thaddeus Farr<br>Offer Certificate › | Ree<br>Norman Ditz<br>Offer Certificate › | Yarn<br>Dorothy Goodman<br>View Decision | Peanut<br>Walter Depp<br>View Decision |
| 📊 Reports | 4:00 PM | CJ<br>Albert & Agnes Finkleman<br>Offer Certificate › | Vargus<br>Brian Trenson<br>Offer Certificate › | Cheddar<br>Lucile & Lou<br>View Decision | Christmas<br>Bob & Darlance Cook<br>Offer Certificate › | Dog<br>Winifred Dundy<br>Offer Certificate › |
| ☐ Start New Claim<br>🎫 Offer Certificate<br>📞 888.733.2670<br>● TRUPANION.COM | 4:30 PM No appointments for that time | | Viola<br>Brian Trenton<br>Start Claim | | Hadley<br>Brian Trenton<br>Claim Processed | |

| Show ● All Claims ○ Open Claims | | Sort by | Submission Date ▽ |
|---|---|---|---|
| Nikko<br>Brian Trenton<br>☐ View Claim Claim# 1006649 invoice# 266379 Payment Date<br>------------------<br>Submitted 10/13/2014 via Trupanion Express | Type Final Invoice | Payee<br>Hospital | In Review |
| Tristan<br>Brian Trenton<br>☐ View Claim Claim# 1006060 invoice# 266379 Payment Date 10/12/2014<br>CONGESTED STUFFY NOSE DIFFICULTY BREATHING ---<br>Submitted 10/11/2014 via Trupanion Express | Type Final Invoice | Payee<br>Client | Claim Processed<br>Pay as Client Paid |
| Wilbur<br>Melly and Tim Ausley<br>☐ View Claim Claim# 1000313 invoice# 265275 Payment Date 10/08/2014<br>------------------<br>Submitted 10/06/2014 via Trupanion Express | Type Final Invoice | Payee<br>Hospital | View Decision<br>$628.82 Trupanion payment |
| Rufus<br>Marin Hardin<br>☐ View Claim Claim# 1000267 invoice# 366273 Payment Date N/A<br>Diarrhea<br>Submitted 10/01/2014 via Trupanion Express | Type Final Invoice | Payee<br>Hospital | View Decision<br>Ineligible |
| Piper<br>Jennifer James<br>☐ View Claim Claim# 1000263 invoice# 206273 Payment Date N/A<br>Diarrhea<br>Submitted 10/11/2014 via Trupanion Express | Type Final Invoice | Payee<br>Client | Claim Processed<br>Pay as Claient Paid |
| Euclid<br>Duity Moore<br>☐ View Claim Claim# 1000259 invoice# 206273 Payment Date 13/08/2014<br>Diarrhea<br>Submitted 10/11/2014 via Trupanion Express | Type Final Invoice | Payee<br>Hospital | View Decision<br>-- Trupanion payment |

FIG. 16

PET INSURANCE SYSTEM AND METHOD

PRIORITY CLAIMS/RELATED APPLICATIONS

This application claims priority under 35 U.S.C. § 120 and is a continuation in part of U.S. patent application Ser. No. 14/924,606, filed on Oct. 27, 2015, now U.S. Pat. No. 10,013,530, issued Jul. 3, 2018, and entitled "Pet Insurance System and Method," which in turn claims priority under 35 U.S.C. § 120 and is a continuation in part of U.S. patent application Ser. No. 14/210,079, filed on Mar. 13, 2014, and entitled "Pet Insurance System and Method," which in turn claims priority to and the benefit under 35 U.S.C. § 119(e) of U.S. Provisional Patent Application Ser. No. 61/801,404, filed on Mar. 15, 2013, and entitled "Pet Insurance System and Method," the entirety of each of which is incorporated herein by reference.

BACKGROUND

Veterinary hospitals provide many medical services during the course of caring for a patient. Pet insurance is one of these many services. Often, patients have health problems that require veterinary care above and beyond what a pet owner is prepared to pay out-of-pocket at the time services are provided, even when they have pet insurance coverage. The pet owner files a claim after leaving the veterinary practice and receives notice of coverage, eligibility and payment, if applicable, from the insurance company. These processes and systems are cumbersome and do not allow a pet owner to rapidly obtain or utilize pet medical insurance.

For the veterinary hospital, existing systems do not provide them with real-time, accurate information about the status of a pet's insurance policy, eligibility of coverage, status of a claim, or facilitate the offering of pet insurance coverage. Most systems are not responsive enough to effectively aid a veterinary practice in managing their practice, frustrating the hospital and the pet owner with the delay.

Additionally, due to the delay in claims processing and the need for the pet owner to cover the expense of medical services at time of service and prior to being reimbursed by the insurance company, the hospital must often provide alternate courses of care that are less expensive, more affordable for pet owners. This is counter-intuitive to the purpose of pet medical insurance coverage.

Thus, it is desirable to provide a pet medical insurance system and method to overcome the above limitations and it is to this end that the disclosure is directed. It is also within the scope of the disclosure to facilitate medical coverage and services at veterinary hospitals outside of pet insurance, such as wellness plans, radiology and lab, and similar services provided at veterinary hospitals utilizing the same system and method implementation.

BRIEF DESCRIPTION OF THE DRAWINGS

The disclosure will be better understood if reference is made to the accompanying drawings, in which:

FIG. 3 illustrates an example of a user interface of the pet medical insurance system;

FIG. 5 illustrates an example of a user interface of appointment data and insurance interaction;

FIG. 7 illustrates an example of a user interface for offering pet insurance coverage to a pet owner;

FIGS. 8A and 8B illustrate an example of a user interface for tracking insurance offers;

FIGS. 11A and 11B illustrate an example of a user interface for medical records requests;

FIGS. 12A and 12B illustrate an example of a user interface for completing medical records requests;

FIGS. 14A and 14B illustrate an example of a user interface for submitting claims in the pet insurance system;

FIG. 15 illustrates an example of a user interface indicating claims outcomes; and FIG. 16 illustrates an example of a user interface for claims submission and payment tracking.

DETAILED DESCRIPTION OF ONE OR MORE EMBODIMENTS

The disclosure is particularly applicable to a cloud computing architecture pet insurance system and it is in this context that the disclosure will be described. It will be appreciated, however, that the system and method has greater utility.

In the disclosure set forth below, a pet owner is a guardian of the pet and could be the pet owner, pet sitter, or similar pet guardian. In the disclosure set forth below, a patient refers to an animal being treated by a veterinary practice. A patient also may be referred to as "pet". In the disclosure below, a veterinary practice refers to a hospital, clinic or similar where services are provided for an animal.

Figure 1:
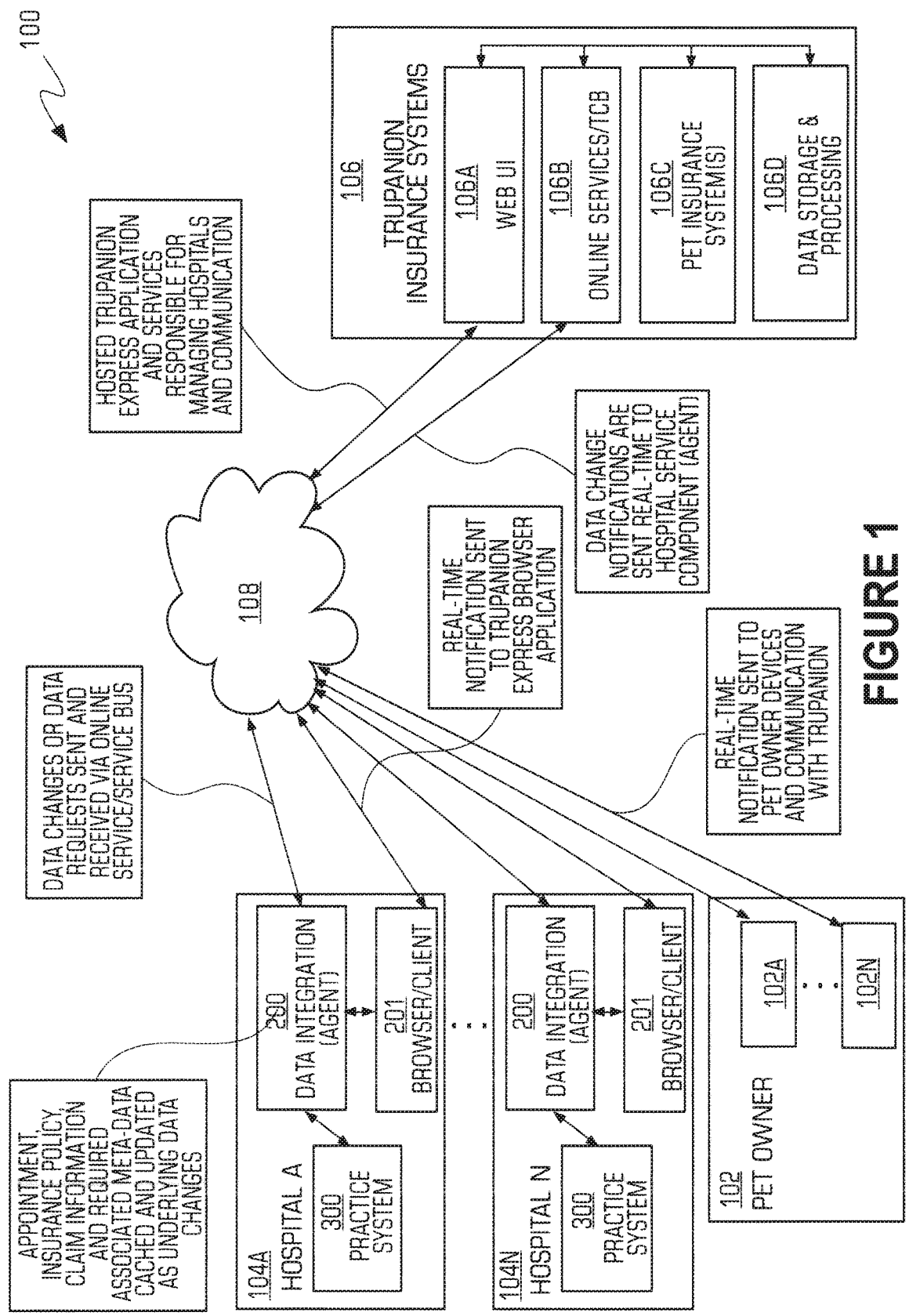
FIG. 1 is a diagram of an implementation of a pet medical insurance system.

FIG. 1 is a diagram of an implementation of pet insurance system 100. The implementation in FIG. 1 is cloud computing architecture. However, the system may be implemented in a client/server architecture, a mainframe architecture, a software as a service model and the like, all of which are within the scope of this disclosure. The system may include one or more computing devices 102, and each computing device may be used by a pet owner to connect to and interact with the pet insurance backend component 106 over a communication path 108. The system may also have one or more computing devices 104 such as 104A, . . . , 104N and each computing device may be used by (or integrated into) a veterinary practice and allow the veterinary practice to interact with a pet insurance backend component 106 or the communications path 108. Each computing device 102, 104 may be a processor based device with storage, memory, a display and wireless or wired connectivity circuits that allow the computing device 102, 104 to interact with the backend component 106. For example, each computing device may be a smartphone device, such as a device operating using the iOS, Android or Symbian operating systems, a personal computer, a client/server system, a terminal, a tablet computer, a cellular phone and any other device that would be capable of interacting with the backend component 106. In one implementation, each of the computing device 104 may have a data integration agent 200 and a client 201 that interacts with the backend component 106. In one implementation, the data integration agent 200 and the client 201 may be a plurality of lines of code executed by the processor of the computing device. In one implementation, each of the computing devices 102, 104 may have a browser that interacts with the backend component 106 displays web pages and allows the user to enter information into forms. In one implementation, the browser may be a plurality of lines of computer code executed by the processor of the computing device 102, 104.

The communication path 108 may be a wired or wireless network that may be unsecure or secure and uses typical protocols for the exchange of data between the computing devices 102, 104 and the backend component 106 For example, the communication path 108 may be an Ethernet network, the Internet, a wireless cellular network, a wireless digital data network and the like or any combination thereof and the system is not limited to any particular communication path 108. In the implementation in which the communication path 108 is the Internet, the communication path 108 may use the known HTTP or HTTPS protocol for data communications.

The backend component 106 may be implemented as one or more computing resources or hardware devices. In one implementation, the backend component 106 may be one or more server computers, one or more cloud computing resources and the like and each resource has one or more processors, memory, persistent storage and the like. The backend component 106 may further comprise a web server 106A online services 106B, a pet insurance management component 106C and data storage and processing 106D that are coupled together as shown in FIG. 1. The web server 106A that may be implemented as a hardware web server or a software implemented web server, may generate and exchange web pages with each computing device 102, 104 that is using a browser. The online services—Trupanion Central Services, or TCS—106B, may be implemented as a plurality of lines of computer code and may generate or exchange information with computing devices 102, 104 directly or through communication path 108 utilizing SignalR, ServiceBus, or similar notification services. The pet insurance management component 106B may be implemented as a plurality of lines of computer code that are stored in the computing resources and then executed by the processor(s) of the computing resources to implement the pet insurance management functions that are described below in more detail. The data processing and storage device 106D may be a hardware storage device or a software implemented storage device, such as a database, that stores user and veterinary practice information for the system, stores information about each insurance offer, stores information about each pet that is enrolled in the pet insurance system, and stores the information about each pet insurance claim in the system.

The communications path 108 can enable exchange of data between different programmatic elements running on the computing devices 102, 104 and different programmatic elements running on the backend server. For example, in each veterinary practice, the respective computing device 104A . . . 104N can comprise a respective data integration agent 200 and browser 201, each of which can independently communicate data using the communication path 108. The communication path enables communication with a plurality of programmatic elements in the backend component 106, including a web server 106A and online services 106B. The web server 106A can include a web user interface configured to exchange information between the computing devices 104A . . . 104N of the respective veterinary practices and the backend component 106. Each of the computing devices 104A . . . 104N can receive information from users in a practice information management system 300 and communicate with the respective data integration agent 200 of the computing device. The data integration agent thus provides a connection between the user information provided to the practice information management system 300 and the backend component 106 via the communications path 108.

As the data integration agent 200 receives information from the practice information management system 300, the data integration agent 200 caches relevant data such as appointment information, insurance policy claim information, and required associated meta-data. This cached information can be updated as the underlying data is changed. When the data changes, the data integration agent 200 can transmit information indicating the data change to the backend component 106. The backend component can transmit data change notifications in real time to the respective computing devices 104A . . . 104N, thereby informing the devices of data changes in real time. The data change notifications can be sent to an express browser application operating on the computing devices 104A . . . 104N. The user device 102 of pet owners can also receive real-time notifications via a web browser interface, allowing the user device to receive data updates in real time as the user device communicates with the backend 106 via the communications path 108.

Figure 2:
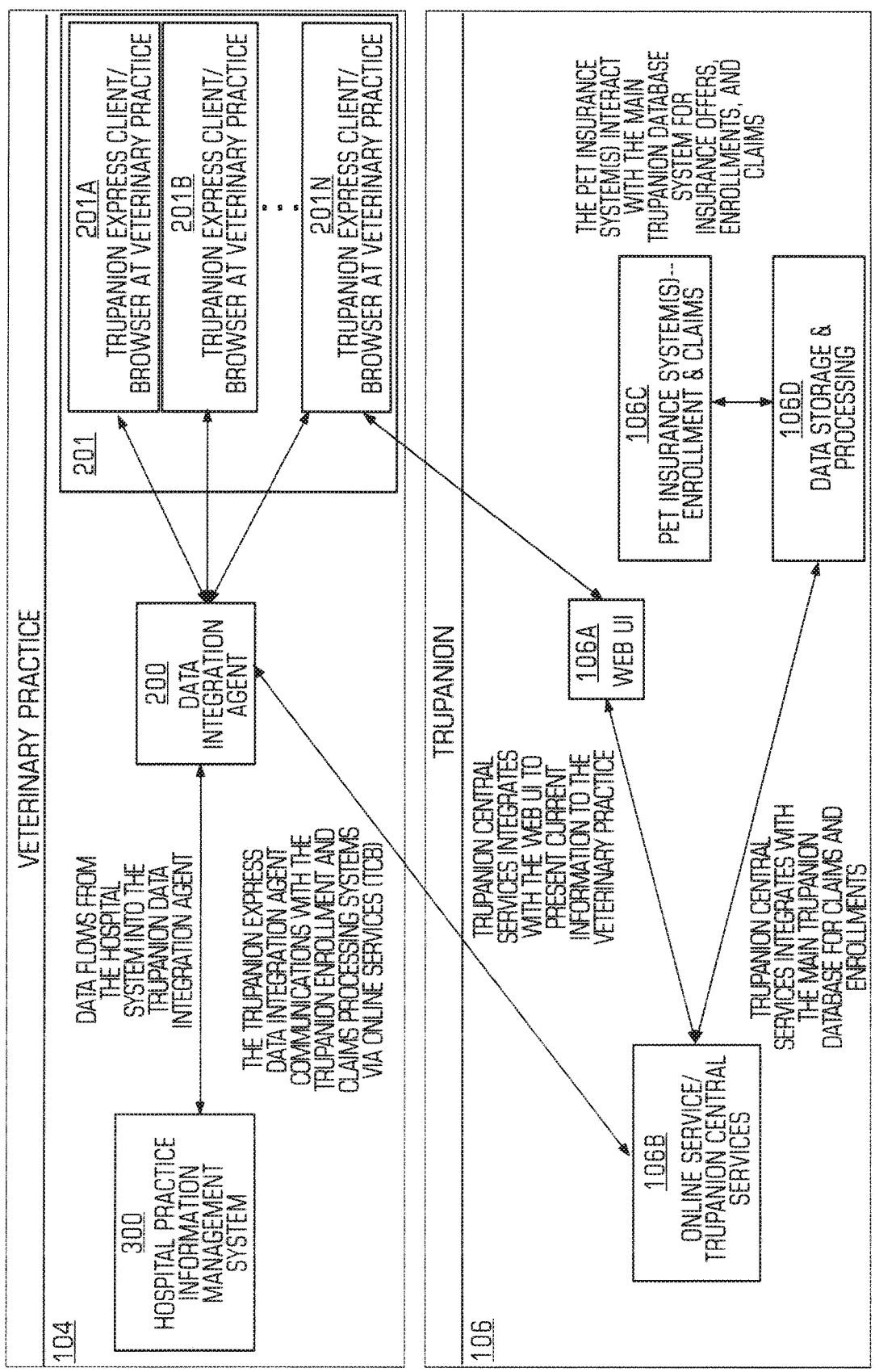
FIG. 2 illustrates more details of the pet medical insurance system.

FIG. 2 illustrates more details of the pet insurance system and in particular the components in each veterinary practice computing device 104 and the backend component 106 and the interactions between the two. As shown the veterinary practice may have one or more browsers/clients 201, a hospital practice information management system 300, and a data integration agent 200. As shown, data from the hospital practice information management system 300 flows into the data integration agent 200 and the data integration agent 200 connects to and communicates with the backend component 106. Online services 106B of the backend component 106 receives the communications from the data integration agent 200, and communicates with the data integration agent 200 as well as the web user interface 106A and a database 106D for data storage and processing. The database 106D is managed using a database system that allows for interactions with a pet insurance system 106C to handle features such as insurance offers, enrollments, and claims. The data integration agent 200 also connects to and communicates with one or more client/browsers 201 in the computing devices 104. In one implementation, each of the components of the veterinary practice computing device 104 may be a plurality of lines of computer code that are executed by a processor of the computing device 104. The Hospital Practice Information Management System (PIMS) is an existing system used by a veterinary practice that use database and visualization technologies (user interface) with the aim to support various hospital/patient management and administration tasks. Different PIMS manufacturers include different modules that allow for many common hospital technology requirements that may include inventory tracking, procedure codes, connection to diagnostic equipment and service providers, connection to a variety of radiology modalities and services, and invoice generation.

The data integration agent 200 may be provided by the pet insurance backend system 106 and may be installed in the computing device 104 of the veterinary practice. The data integration agent 200 is a system which integrates with these varied systems to provide added value and operational simplicity for employees of the veterinary practice and pet owners. The data integration agent is responsible for retrieving and mapping data from the PIMS 300, sending communications to and receiving information from Trupanion Central Services 106B about claim, insurance offers, and enrollments, and communication with the Trupanion Express clients/browsers 201. The data integration agent 200 employs various technological mechanisms to limit traffic between Trupanion Central Services 106B and Trupanion Express clients/browsers 201, as well as the PIMS 300, creating efficient correspondence between all systems. The data integration agent 200 may include an abstracted engine that allows communication with various PIMS systems on the market today, as well as the ability to integrate with additional in the future in a plug-and-play fashion.

The client/browser 200, is the user interface for Trupanion Express. It communicates with the data integration agent 200 and the web UI 106A with the aim to exchange information between the hospital and the backend component 106. Integrating services provided by the backend system 106 via the web user interface 106A allows the system to provide veterinary practices with current, real-time access to information stored in the backend system 106. The client/browser allows submitting claims, issuing insurance offers, searching PIMS data for clients, appointments, mapping clients between systems, and displaying all of the information for these activities in a digestible way for veterinary practice employees—resulting in improved patient care.

The backend component 106 may further comprise a services component 106B, that may be known as Trupanion Central Services, a data storage and processing component 106D, and a pet insurance system(s) 106C, that may be comprised of enrollment and claims systems that are coupled together as shown in FIG. 2. Sample data is included in the below table:

| Sample Data Exchanged Between the Veterinary Practice & Trupanion | Enrollment Sample Data | Claims Sample Data |
| --- | --- | --- |
| Patient demographics | Policy ID & type | Claims basics |
| Client demographics | Policy status | Claiming veterinary practice information |
| Claim form information | Enrollment veterinary practice information | Claim outcomes & amount covered |
| Invoices/estimates | Policy coverage details | Claims payments |
| Medical record information | | |
| Insurance offer information | | |

In one implementation, each of the components of the backend 106 may be a plurality of lines of computer code that are executed by a processor of the computing device 106. The services component 106B integrates with data storage and processing 106D. The enrollment processing system and claims processing system—pet insurance systems 106C—may interact with the data storage and processing systems 106D allowing insurance offers to be issued and activated and claims to be processed. The services component 106B is a service inside Trupanion's network and processes requests from and sends information to the data integration agent 200 and passes appropriately formed requests to the data storage & processing systems 106D. The data storage and processing system 106D is any location where transactional data for Trupanion's various IT systems is processed and/or stored. The pet insurance system 106C is comprised of the enrollment processing system, the system that issues insurance offers to pet owners, and the claims processing system, the system that catalogs the collection of medical records that enables claims adjudicators to manage and process pet owner claims. The pet insurance system 100 is revolutionary in that it enables claims to be adjudicated very quickly—allowing the pet owner to not pay out-of-pocket expenses at the veterinary practice. Said another way, the pet insurance system 100 allows Trupanion to pay the veterinary hospital directly with the invoice while the customer is waiting to checkout, similar to the concept of "co-pay" in human health care. The pet insurance system 100 allows for near real-time claims submission and claims processing, enabling claim adjudication at point-of-sale at the veterinary practice. A typical system uses typical channels such as fax or mail that support a delayed reimbursement model for veterinary practices and/or pet owners.

Figure 3:
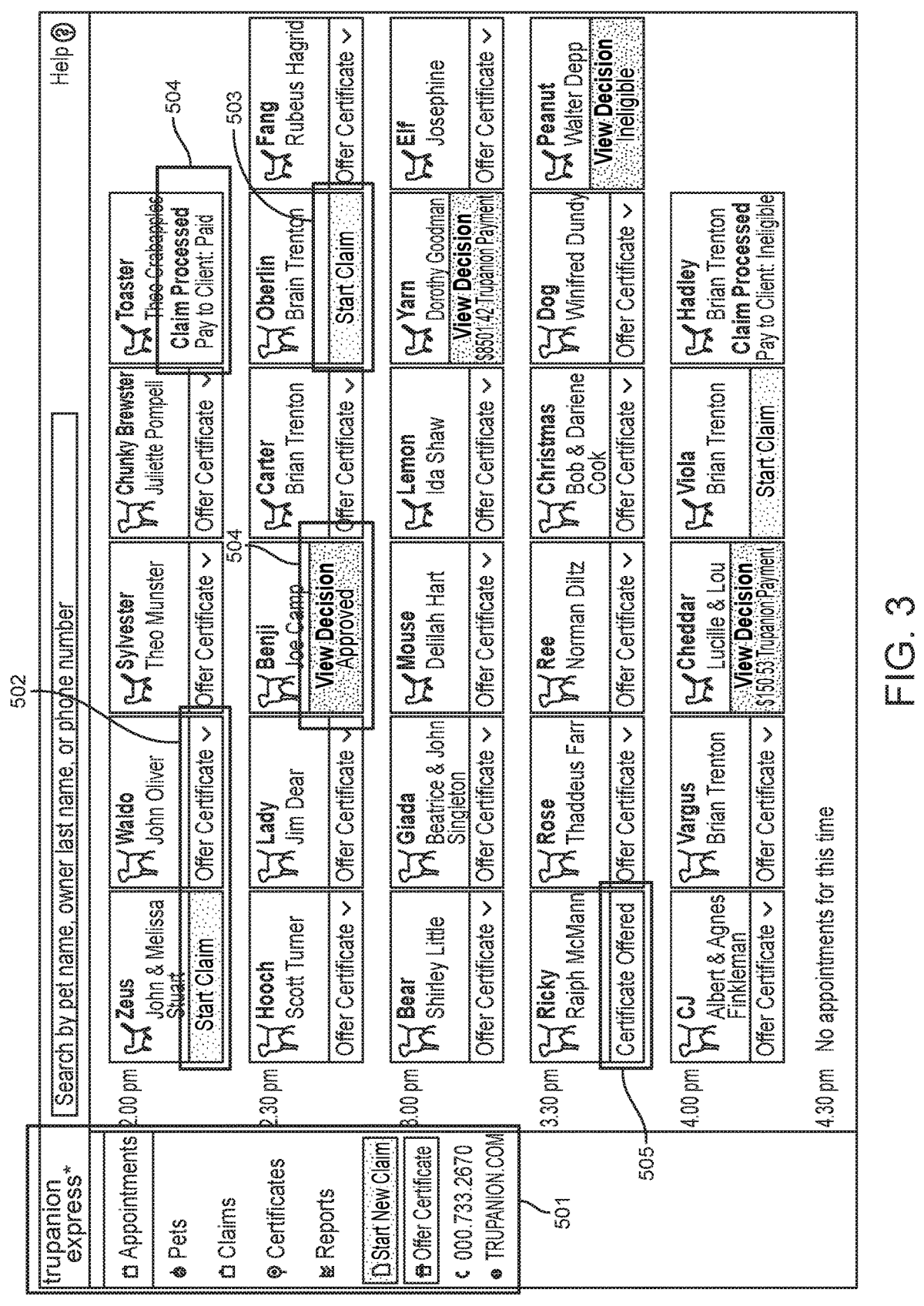

FIG. 3 illustrates an example of a user interface 500 of the pet insurance system. The user interface may include a navigation portion 501 that allows the user to navigate around to various parts of the pet insurance system user interface. The user interface may include a status 502 for each pet to indicate the current coverage of that pet. The user interface may further include an action button 503 allowing the user to submit claims or issue an insurance offer to a selected pet. The user interface may have status indicators for current claims transactions 504. The user interface may also have status indicators for current offers of insurance 505.

Figure 4:
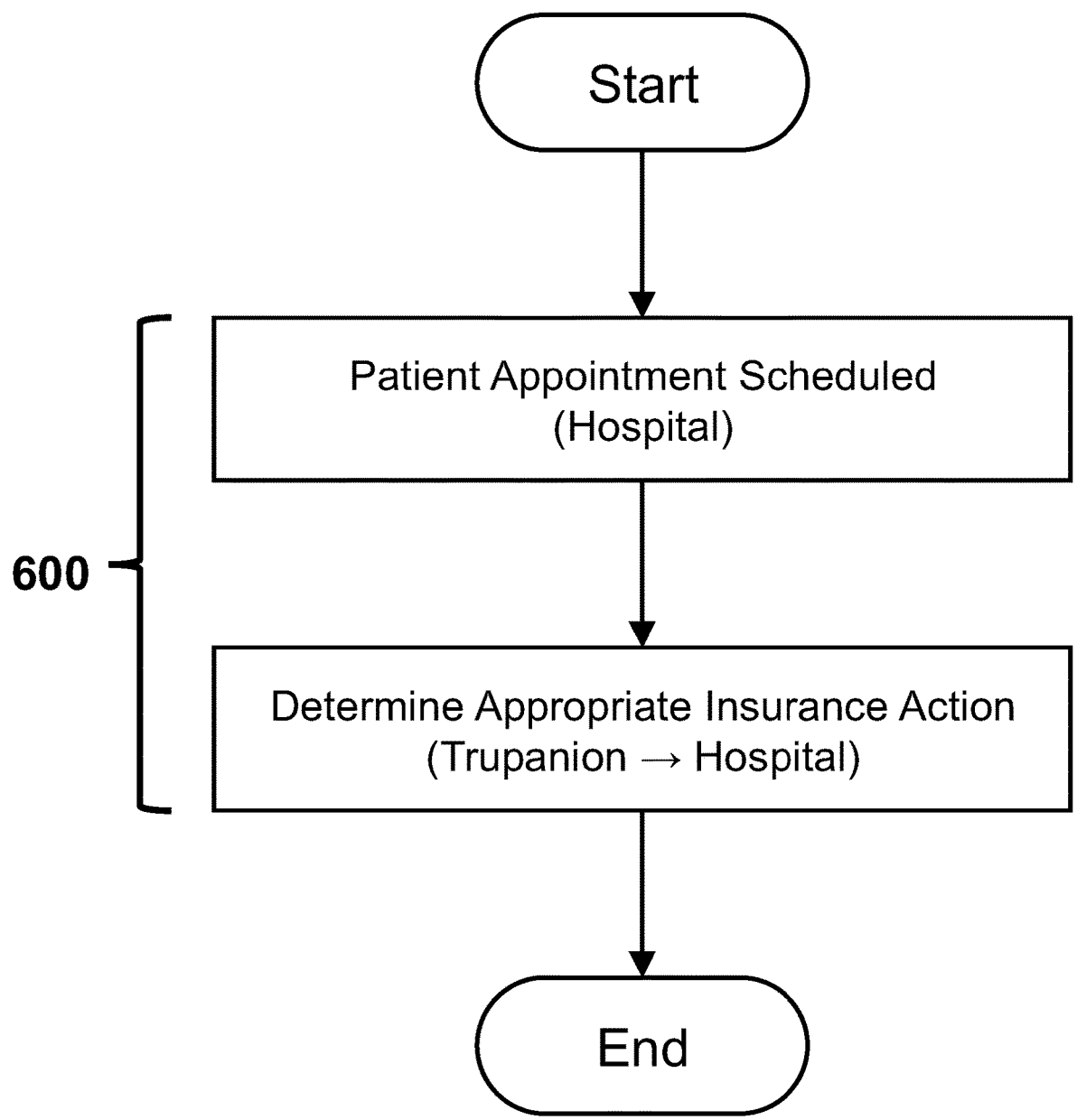
FIG. 4 illustrates a method of interacting with hospital appointment information and providing insurance action options.
Figure 5:
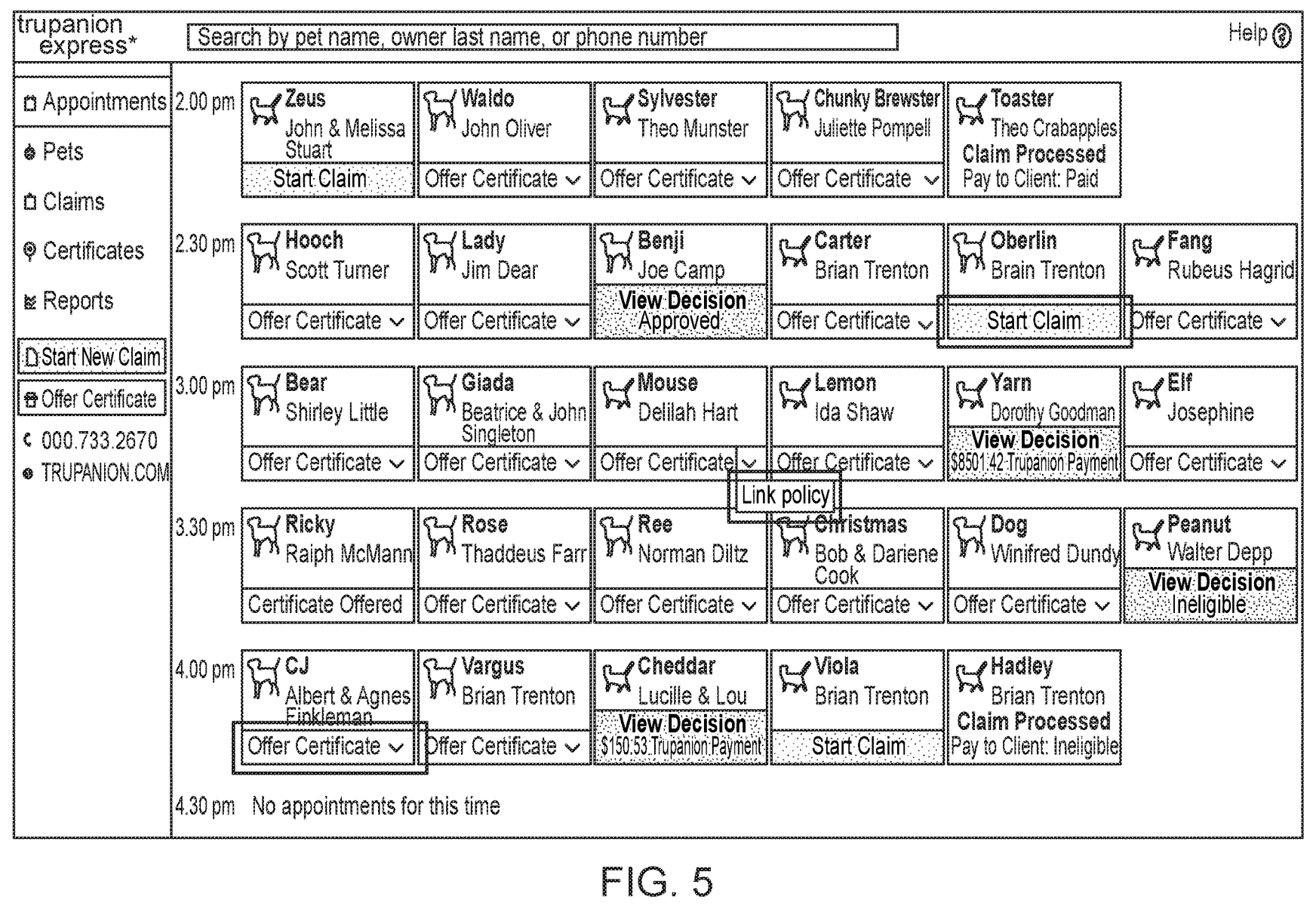

FIG. 4 illustrates a method 600 for determining the current pet insurance coverage for patient with scheduled appointments in the hospital practice information management system 300 and displaying the appropriate action in the pet insurance system user interface 500. FIG. 5 illustrates an example of a user interface displaying the appropriate insurance based on the method illustrated in FIG. 4.

Figure 6:
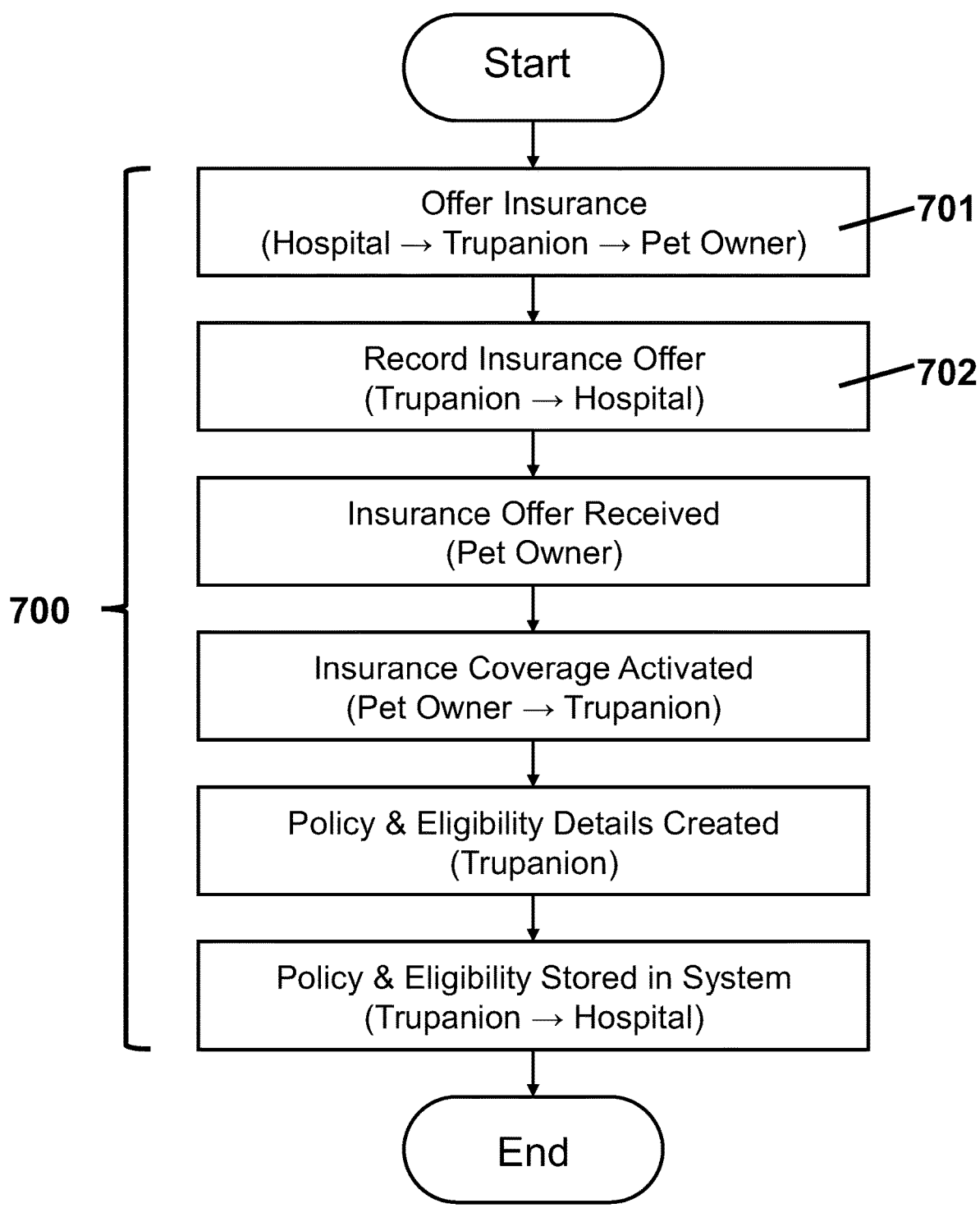
FIG. 6 illustrates a method for offering insurance, tracking insurance offers, and providing insurance coverage and eligibility details.

FIG. 6 illustrates a method 700 for obtaining insurance and tracking insurance offers using the pet insurance system and FIG. 7 illustrates an example of a user interface for offering pet insurance to a pet owner. The pet insurance system makes it easier for a pet owner to get pet insurance and then quickly be able to have proof of the pet insurance in the form of an insurance offer that can be presented to the veterinary practice to establish the insurance of the pet. In the method 700, a veterinary practice may provide a pet owner an insurance offer 701 which is recorded in Trupanion systems 702 through the data integration agent 200. When the veterinary practice offers the insurance to the pet owner, an employee of the veterinary practice may enter the insurance offer into the client 201, such as shown in FIG. 7, and the information about the insurance offer is passed onto the backend component 106 through the data integration agent 200. The pet owner, using a computing device 102, can receive the insurance offer and may then activate the insurance offer, and obtain pet insurance, using an email link or by phone which is sent to the backend component 106. Once the pet owner activates the insurance coverage, policy and eligibility details are created and stored in the system, and the pet owner receives proof of insurance which is also passed back to the veterinary practice through the data integration component 200 so that the veterinary practice receives quick notice of the insurance for the pet. In addition, since the computing device 104 and the backend component 106 are integrated as shown in FIG. 2, all parties involved are rapidly notified of changes to the pet's insurance coverage. For example, this means the veterinary practice can be comfortable that the pet has insurance for the procedure that is about to be performed. The system may also display the treatment or procedure that is, has been or will be performed on a particular patient or by a particular employee at the veterinary practice.

Figure 8A:
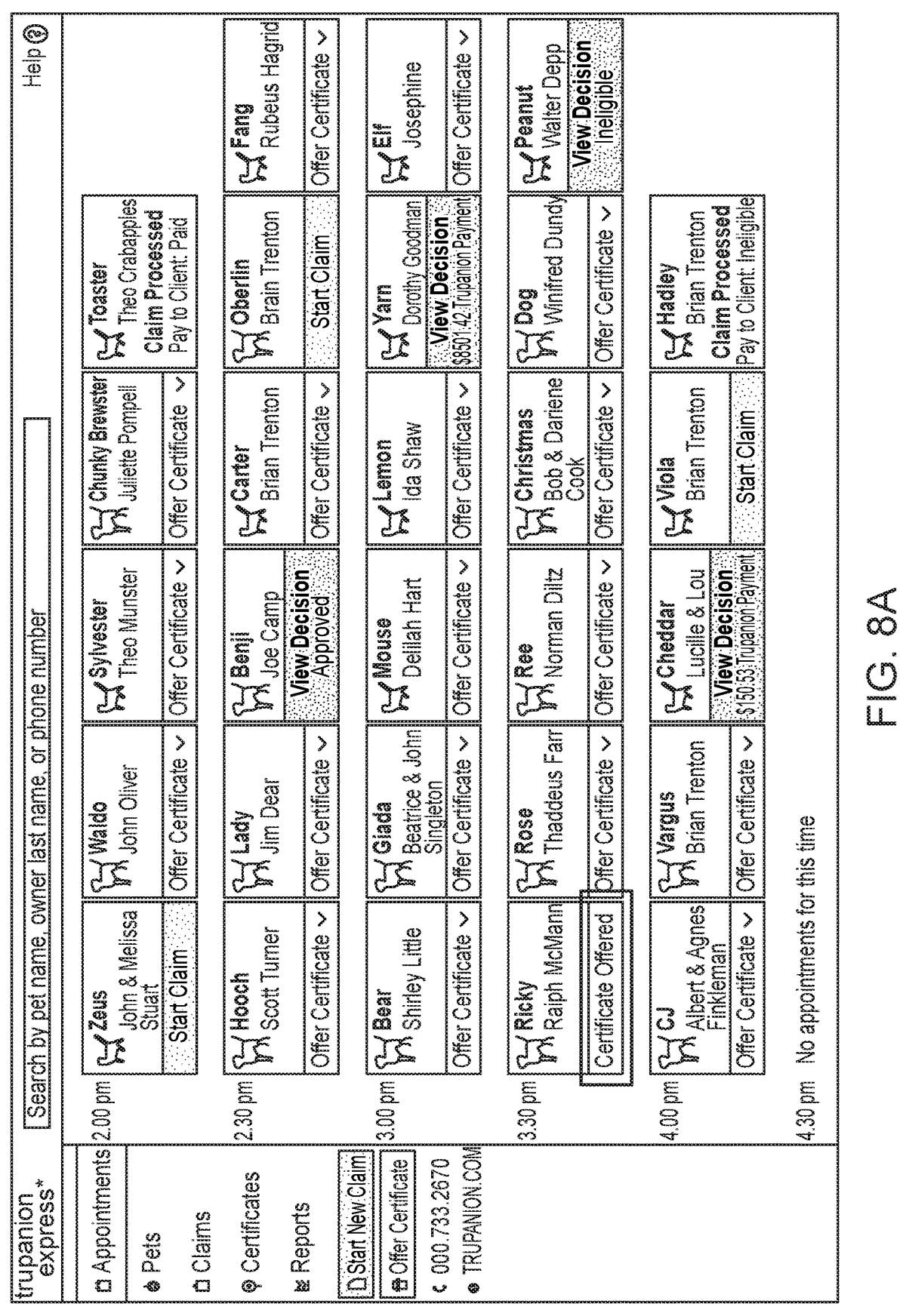
Figure 9:
FIG. 9 illustrates an example of a user interface displaying the status of a particular pet's medical insurance coverage and eligibility.

FIGS. 8A and 8B illustrate examples of a user interface for tracking pet insurance offers through the pet insurance system user interface in the client/browser 201 in the veterinary practice. FIG. 9 illustrates an example of a user interface of a particular pet's insurance coverage eligibility once the insurance offer has been activated.

Figure 10:
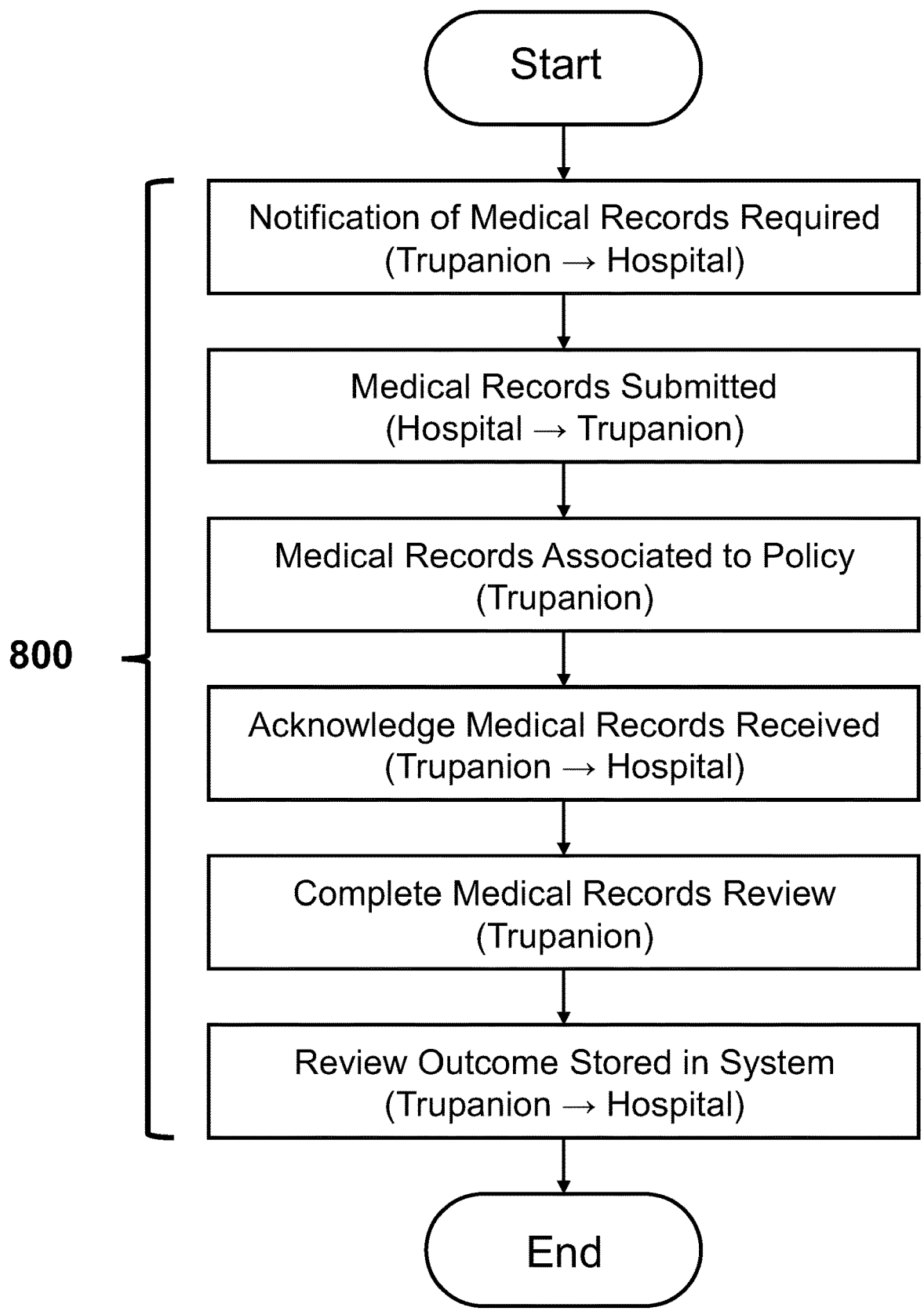
FIG. 10 illustrates a method for requesting and receiving medical record information.
Figure 11A:
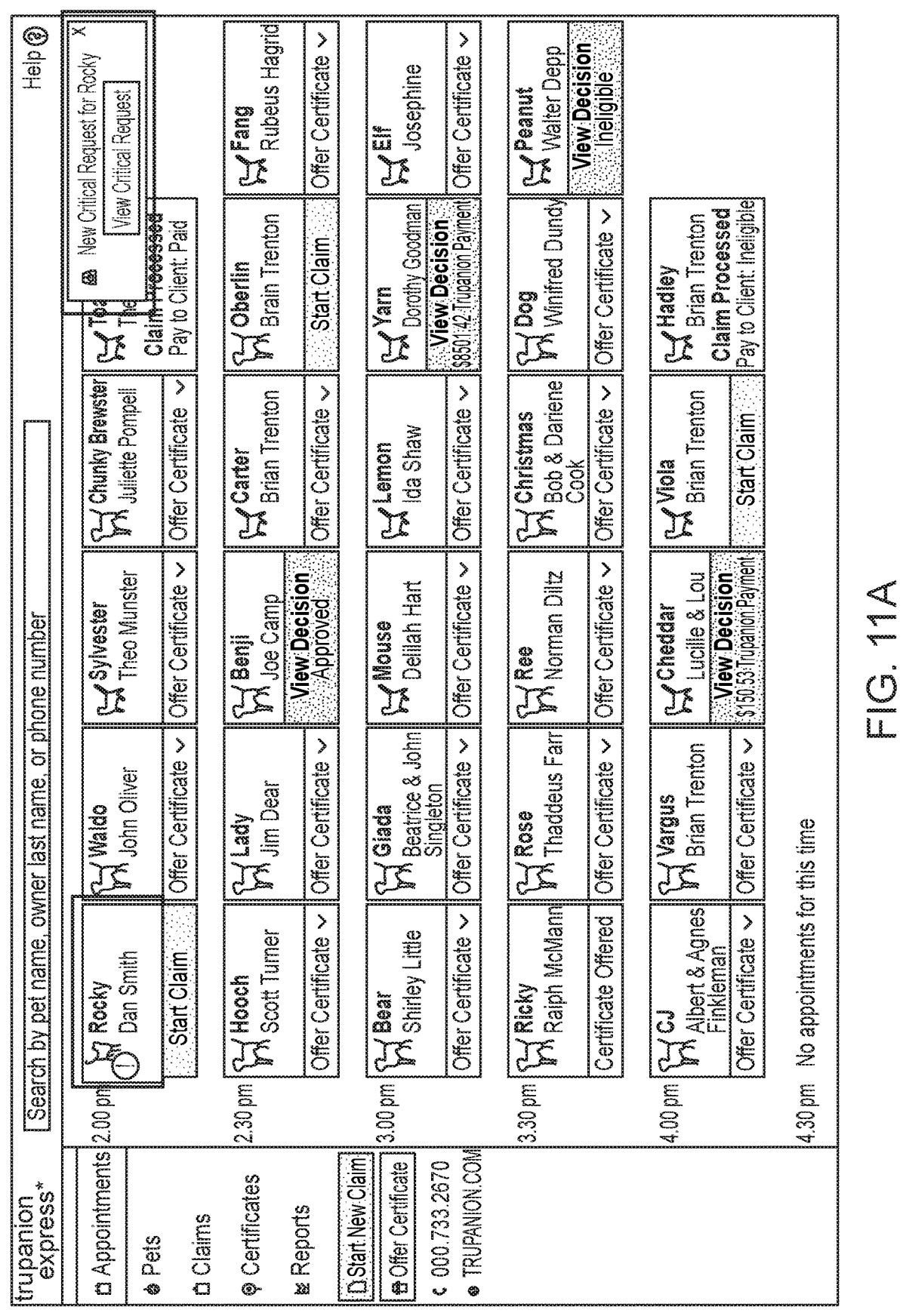
Figure 11B:
Figure 12B:
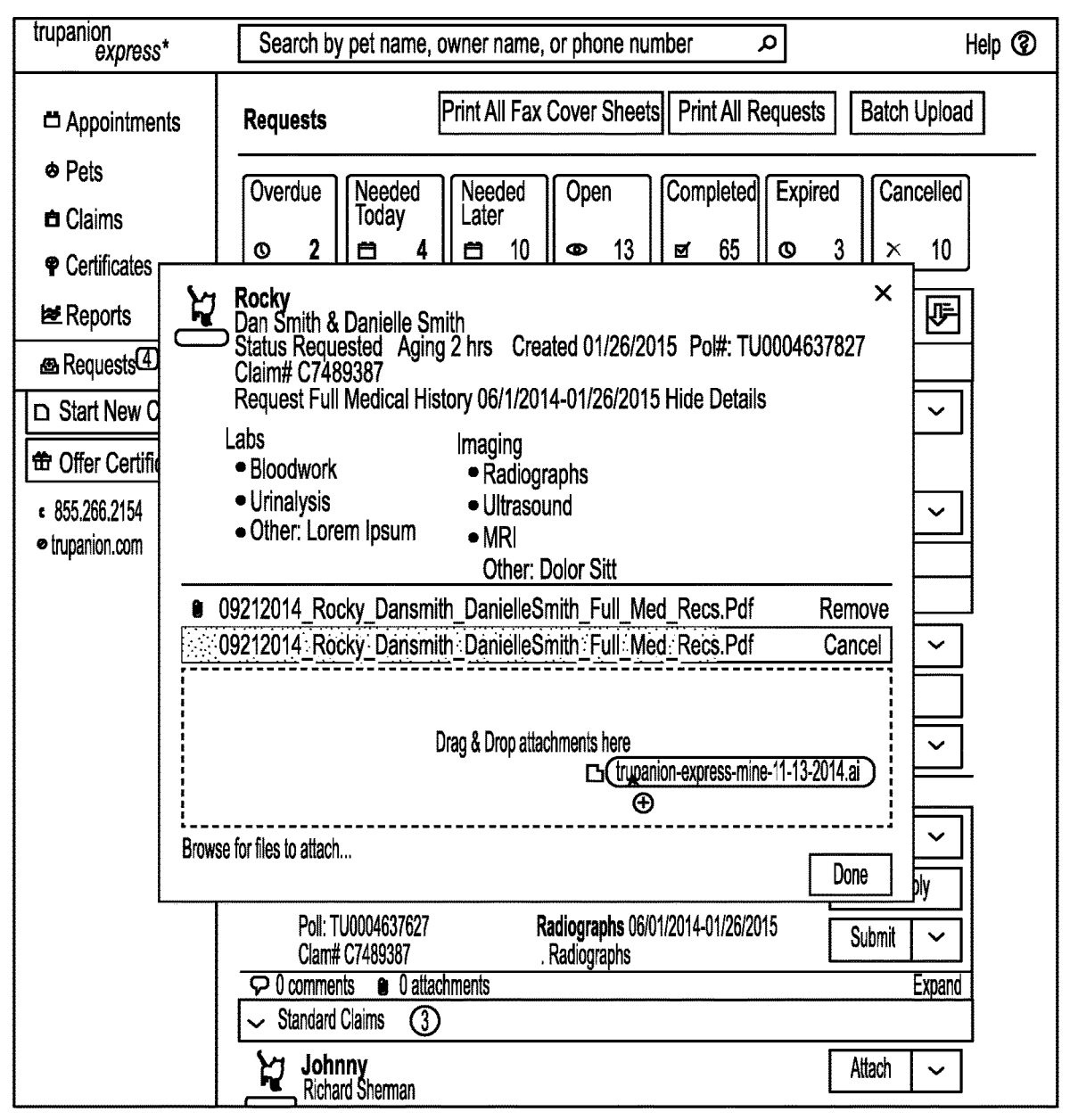

FIG. 10 illustrates a method 800 for requesting and receiving medical record information used to determine a pet's eligibility for insurance coverage. When the pet insurance system is generating the eligibility the computing device 200 and the pet insurance systems 106C may obtain a history of a pet from any veterinary practice that has seen the pet in the past through the data integration component 200. The pet insurance components 106C may then structure that data and generate an eligibility of coverage. The system may then display that eligibility of coverage to the users of the system which allows all of the users to rapidly see the coverage status for a pet in a user interface (refer to FIG. 9). During the course of collecting medical record information for a pet, it may be required for a hospital to respond directly to requests for information utilizing the user interface of the pet insurance system. FIGS. 11A and 11B illustrate an example of a user interface for notification of a request for medical records and tracking of medical records requests. FIGS. 12A and 12B illustrate an example of a user interface for submitting requested records and completing medical records requests.

Figure 13:
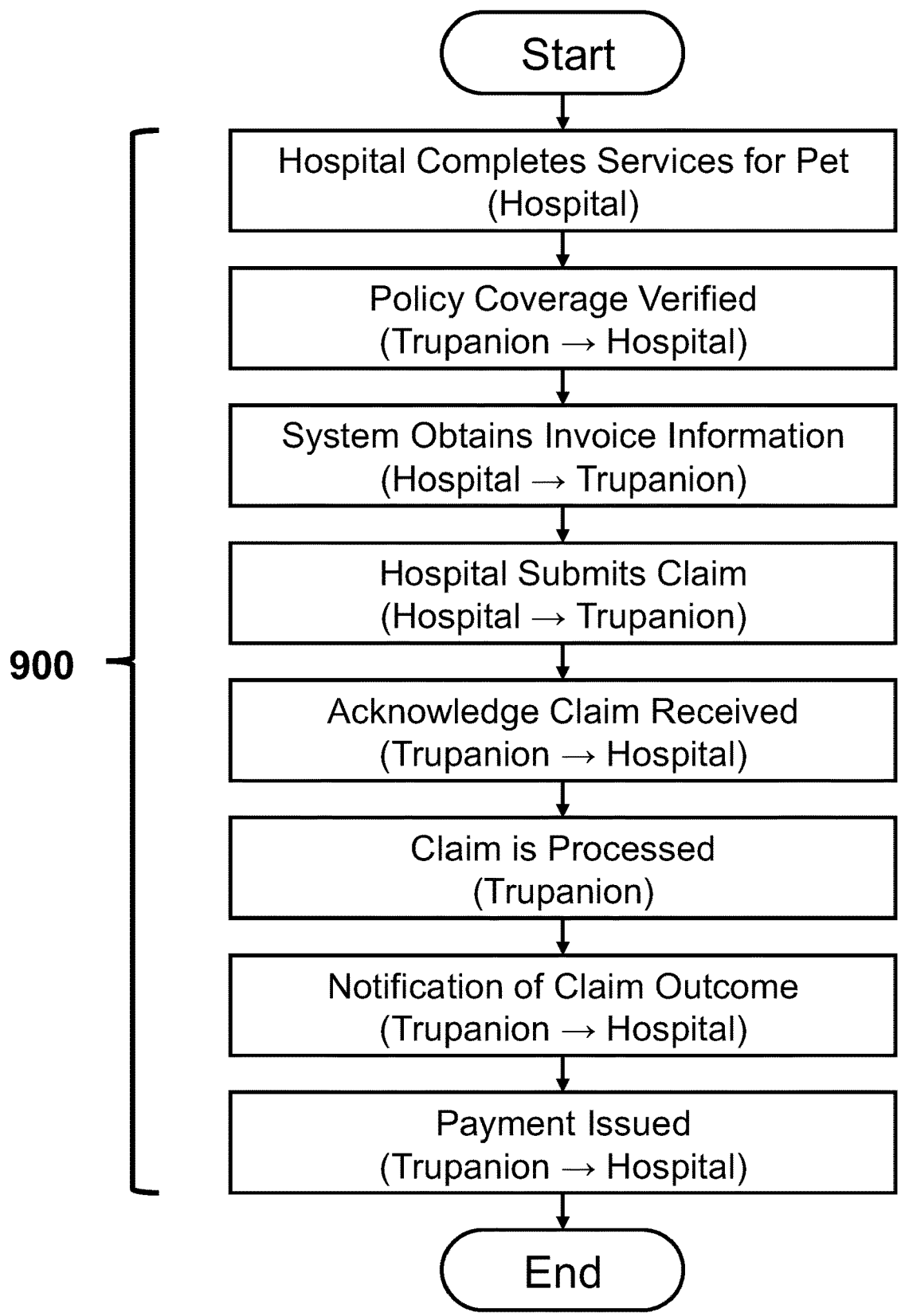
FIG. 13 illustrates a method for submitting and processing a claim in the pet insurance system.
Figure 14B:
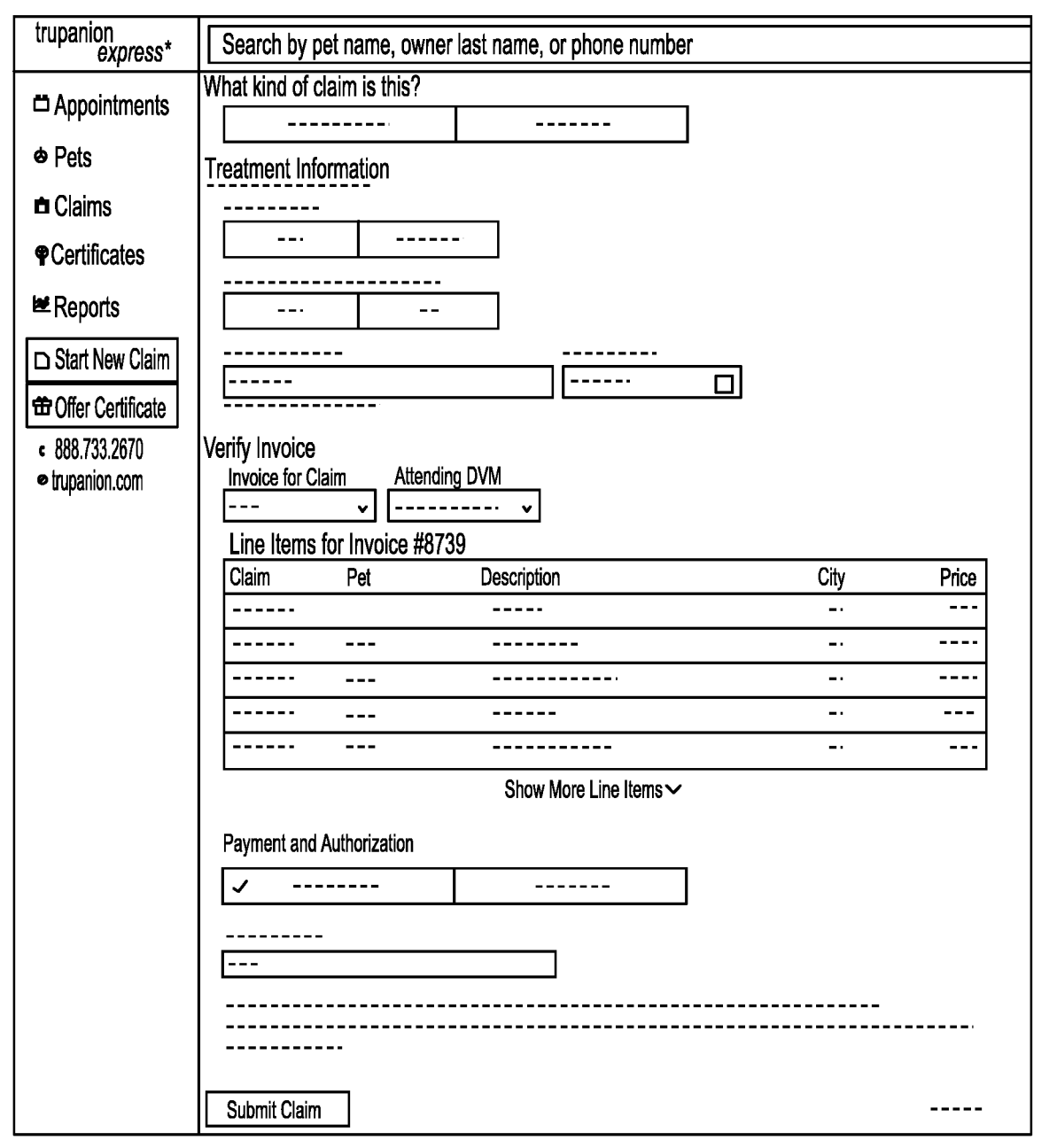

FIG. 13 illustrates a method 900 for submitting and processing a claim in the pet insurance system. Since the backend component and each computing device in the veterinary practice are integrated, as seen in FIG. 2, and the system has determined a patient's eligible coverage, an insurance claim may be quickly processed by the claims processing component of the pet insurance component 106C. A claim starts when an employee or doctor of a veterinary hospital completes services for a pet. The policy coverage can be verified by the data integration agent 200, which can indicate the verification to the veterinary practice. The system can obtain invoice information from the veterinary practice, which may be sent to the data integration agent 200. The veterinary practice submits a claim (see FIG. 14A for an example) for the treatment using a claim form (such as shown in FIG. 14B) that is generated by the client/browser 201 in combination with the data integration agent 200. The receipt of the claim by the data integration agent 200 can be acknowledged to the veterinary practice. The pet insurance company, through the pet insurance systems 106C, may then process the claim. The pet insurance company has the status of the pet's eligibility for coverage and this is able to quickly approve or deny the insurance claim for the pet. If the claim is approved, the claim may be paid directly to the veterinary practice (in one implementation, electronically via ACH) and then the pet owner pays their portion to the veterinary practice. In this manner the system allows a claim to be quickly processed and then paid if the insurance claim is approved.

Figure 15:
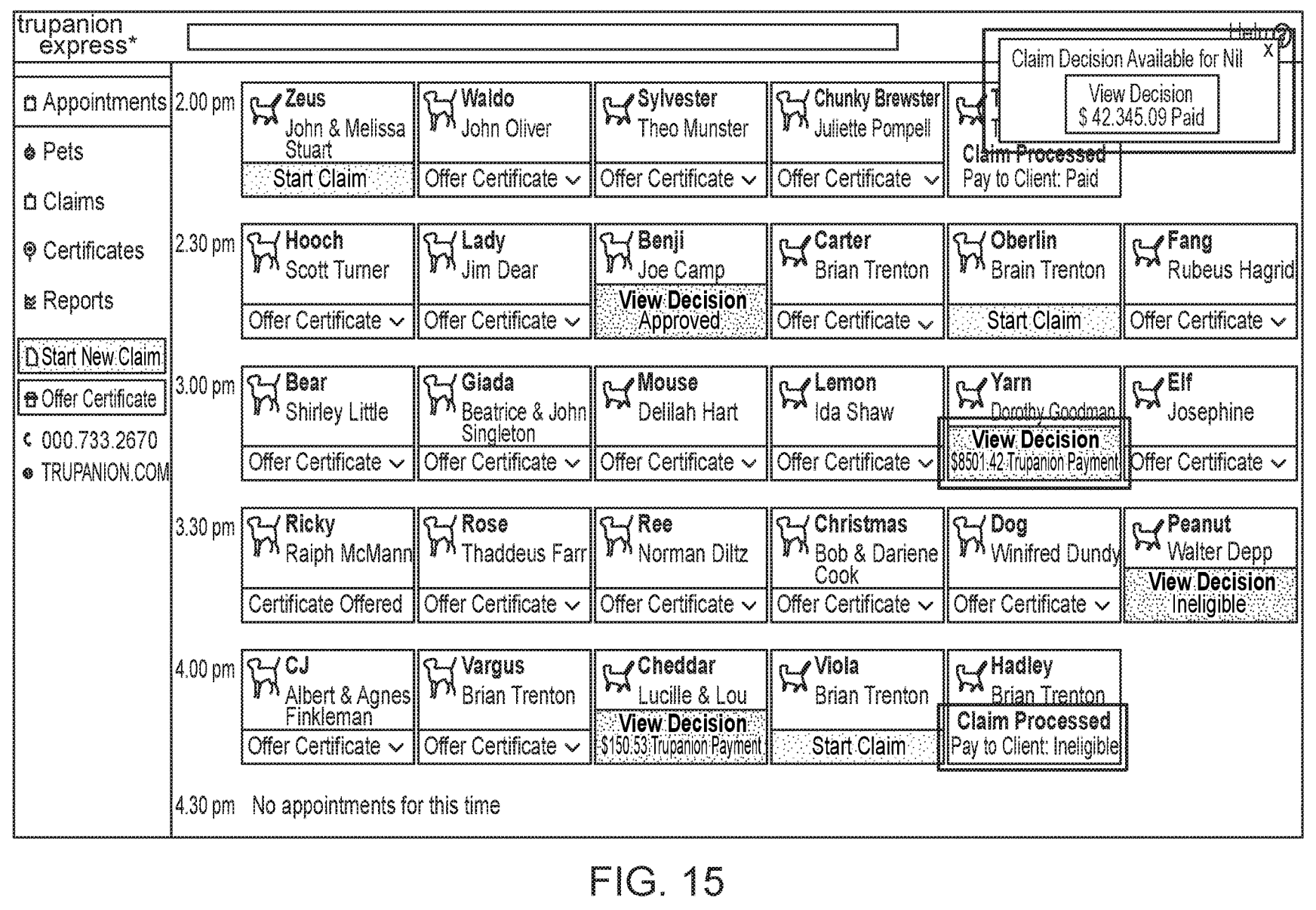

FIG. 15 is an example of a user interface of pet insurance system 100 highlighting display of communication from Trupanion to the veterinary practice claim outcome information.

FIG. 16 is an example of a user interface for pet insurance system 100 for tracking of the status of claims submitted and the outcomes and payments for those claims.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A pet medical insurance system, comprising:
a backend component implemented on a computer, the backend component comprising a services component;
a pet insurance component in a veterinary practice comprising a practice management system;
a plug-and-play data integration system connected to the pet insurance component of the veterinary practice and in communication with the backend component, wherein the plug-and-play data integration system receives data from the pet insurance component, maps the data according to the backend component and sends the mapped data to the backend component, thereby limiting the data traffic between the backend component and the pet insurance component, the plug-and-play data integration system being plug-and-play integratable with a second or more different practice management systems for connection thereto;
wherein the data comprises, one or more pieces of information about one or more treatments and procedures for a patient by the veterinary practice;
the backend component further comprising an enrollment processing component and a claim processing component, the enrollment processing component configured to receive a request for insurance coverage for the patient and issue an insurance offer to an owner of the patient; and
the claim processing component configured to process a claim for one or more treatments and procedures for the patient and pay an amount to the veterinary practice;
wherein the claim processing component processes the claim so that the veterinary practice is informed of the pay amount.

2. The system of claim 1, wherein the backend component further comprises a user interface component that is configured to generate a user interface containing information about the patient for the veterinary practice.

3. The system of claim 1, wherein the backend component further comprises one or more databases that store the one or more pieces of information about one or more of treatments and procedures for the patient by the veterinarian or an employee of the veterinary practice.

4. The system of claim 2, wherein the user interface component is configured to generate an insurance claim form.

5. The system of claim wherein the backend component further comprises one or more computing resources that host the backend component.

6. The system of claim 5, wherein each of the one or more computing resources is one of a server computer and/or cloud computing resource(s).

7. A method of providing pet medical insurance using a backend component implemented on a computer, comprising:
receiving, by a services component of the backend component from a first veterinary practice system that is remote from the backend component, one or more pieces of data about one of a treatment and procedure for an animal;
mapping data from the first veterinary practice system to the services component by a plug-and-play data integration system connected to the first veterinary practice system and in communication with the backend component, the plug-and-play data integration system comprising:

receiving data from the first veterinary practice system;

mapping the data according to the services component; and sending the mapped data to the services component, thereby limiting the data traffic between the services component and the first veterinary practice system to create efficient correspondence between the services component and the first veterinary practice system, the plug-and-play data integration system being plug-and-play integratable with a second or more veterinary practice systems for connection thereto;

enrolling, by an enrollment processing component, an owner of the animal for pet medical insurance for the animal upon receipt of a request for the pet medical insurance of the animal and issuing an insurance offer for the animal; and processing, using a claim processing component of the backend component, a claim for one of the treatment and procedure for the animal, wherein the claim processing component processes the claim and pays a veterinary practice.

8. The method of claim 7 further comprising generating a user interface containing information about the animal.

9. The method of claim 7 further comprising storing the one or more pieces of data about one of the treatment and procedure for the animal.

10. The method of claim 8 further comprising generating an insurance claim form.

11. The method of claim 7, wherein enrolling the owner of the animal further comprises activating the offer for insurance coverage.

12. A pet insurance system, comprising:

a veterinary practice system having a pet insurance component;

a backend component comprising a services component that is configured to be coupled to and communicate with the pet insurance component in each veterinary practice over a communications path and via a plug-and-play data integration system, wherein the services component receives, from the pet insurance component over the communications path, one or more pieces of data about one of a treatment and a procedure for an animal by a veterinary practice, and the plug-and-play data integration system maps the one or more pieces of data about one of the treatment and the procedure from the pet insurance component according to the backend system, thereby limiting data traffic between the backend component and the pet insurance component, the plug-and-play data integration system being plug-and-play integratable with a second or more different veterinary practice systems for connection thereto;

the backend component further comprising an enrollment processing component and a claim processing component, the enrollment processing component configured to receive a request for the animal and issue an insurance offer to an owner of the animal for insurance for the animal and the claim processing component configured to process a claim for one of the treatment and the procedure for the animal and pay an approved claim amount to the veterinary practice; and wherein, the claim processing component processes the claim so that the veterinary practice is paid.

13. The system of claim 12, wherein the backend component further comprises a user interface component that is configured to generate a user interface containing information about the animal for the veterinary practice.

14. The system of claim 12, wherein the backend component is configured to generate an insurance claim form.

15. The system of claim 13, wherein the user interface component is configured to generate an insurance claim form.

16. The system of claim 12, wherein the backend component further comprises one or more computing resources that host the backend component.

17. The system of claim 16, wherein each of the one or more computing resources is one of a server and/or cloud computing resource(s).

18. The system of claim 12 further comprising one or more computing devices wherein each computing device is configured to allow the owner of the animal to activate insurance coverage.

19. The system of claim 18, wherein each computing device further comprises a processor and a browser application executed by the processor to interact with the backend component.

* * * * *